(12) United States Patent
Burright et al.

(10) Patent No.: US 8,969,397 B2
(45) Date of Patent: *Mar. 3, 2015

(54) SYSTEMS AND METHODS TO TREAT PAIN LOCALLY

(75) Inventors: Eric N. Burright, Eagan, MN (US); Lisa L. Shafer, Stillwater, MN (US); Bill McKay, Memphis, TN (US); John Zanella, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 265 days.

This patent is subject to a terminal disclaimer.

(21) Appl. No.: 12/701,261

(22) Filed: Feb. 5, 2010

(65) Prior Publication Data

US 2010/0159015 A1    Jun. 24, 2010

Related U.S. Application Data

(63) Continuation of application No. 11/460,012, filed on Jul. 26, 2006, which is a continuation-in-part of application No. 10/972,157, filed on Oct. 22, 2004, now abandoned.

(51) Int. Cl.
| | |
|---|---|
| *A61K 31/4168* | (2006.01) |
| *A61K 31/00* | (2006.01) |
| *A61K 9/00* | (2006.01) |
| *A61K 9/16* | (2006.01) |
| *A61K 31/185* | (2006.01) |
| *A61K 31/192* | (2006.01) |
| *A61K 31/352* | (2006.01) |
| *A61K 31/366* | (2006.01) |
| *A61K 31/381* | (2006.01) |
| *A61K 31/401* | (2006.01) |
| *A61K 31/4402* | (2006.01) |
| *A61K 31/498* | (2006.01) |
| *A61M 37/00* | (2006.01) |

(52) U.S. Cl.
CPC ............... *A61K 31/00* (2013.01); *A61K 9/0019* (2013.01); *A61K 9/0024* (2013.01); *A61K 9/1647* (2013.01); *A61K 31/185* (2013.01); *A61K 31/192* (2013.01); *A61K 31/352* (2013.01); *A61K 31/366* (2013.01); *A61K 31/381* (2013.01); *A61K 31/401* (2013.01); *A61K 31/4168* (2013.01); *A61K 31/4402* (2013.01); *A61K 31/498* (2013.01); *A61M 37/0069* (2013.01); *G01N 2800/2842* (2013.01)
USPC ........... 514/385; 514/275; 514/277; 514/311; 514/419; 514/423; 514/460; 514/529

(58) Field of Classification Search
CPC . A61K 31/40; A61K 31/405; A61K 31/4168; A61K 31/44; A61K 31/47; A61K 47/48369; A61K 9/1647
USPC .......... 424/424, 489; 514/275, 277, 311, 419, 514/423, 460, 529, 385
See application file for complete search history.

(56) References Cited

U.S. PATENT DOCUMENTS

| | | | |
|---|---|---|---|
| 4,692,147 | A | 9/1987 | Duggan |
| 5,711,316 | A | 1/1998 | Elsberry et al. |
| 5,801,188 | A | 9/1998 | Hassenbusch |
| 5,978,702 | A | 11/1999 | Ward et al. |
| 5,980,927 | A * | 11/1999 | Nelson et al. ................. 424/425 |
| 6,093,180 | A | 7/2000 | Elsberry |
| 6,180,355 | B1 | 1/2001 | Alexander et al. |
| 6,521,259 | B1 * | 2/2003 | Chasin et al. ................. 424/489 |
| 6,594,880 | B2 | 7/2003 | Elsberry |
| 6,596,747 | B2 | 7/2003 | Bos |
| 6,902,910 | B2 | 6/2005 | Ni et al. |
| 7,993,666 | B2 * | 8/2011 | McKay et al. ................. 424/424 |
| 2002/0071822 | A1 | 6/2002 | Uhrich |
| 2003/0049256 | A1 | 3/2003 | Tobinick |
| 2003/0077641 | A1 | 4/2003 | Laskowitz et al. |
| 2003/0119017 | A1 | 6/2003 | McSwiggen |
| 2003/0157061 | A1 | 8/2003 | Bennett |
| 2003/0175793 | A1 | 9/2003 | Bennett et al. |
| 2003/0185826 | A1 | 10/2003 | Tobinick |
| 2004/0034357 | A1 | 2/2004 | Beane et al. |
| 2004/0052384 | A1 | 3/2004 | Ashley |
| 2004/0265364 | A1 | 12/2004 | Ozturk et al. |
| 2005/0058696 | A1 * | 3/2005 | Donello et al. ............... 424/449 |
| 2005/0075701 | A1 | 4/2005 | Shafer |
| 2005/0090549 | A1 | 4/2005 | Hildebrand et al. |
| 2005/0095246 | A1 | 5/2005 | Shafer |
| 2005/0129731 | A1 | 6/2005 | Horres et al. |
| 2005/0180974 | A1 | 8/2005 | Shafer |

(Continued)

FOREIGN PATENT DOCUMENTS

| | | |
|---|---|---|
| EP | 1 405 646 A2 | 4/2004 |
| EP | 1462111 A1 | 9/2004 |

(Continued)

OTHER PUBLICATIONS

Mercadante et al. Support. Care Cancer, vol. 7, 1999, pp. 47-50.*

(Continued)

*Primary Examiner* — Jeffrey Stucker
*Assistant Examiner* — Stephen Gucker
(74) *Attorney, Agent, or Firm* — Sorell Lenna & Schmidt LLP

(57) ABSTRACT

Disclosed herein are systems and methods for contributing to the local treatment of pain. More specifically, the disclosed systems and methods contribute to the local treatment pain by inhibiting the NFκB family of transcription factors.

14 Claims, 5 Drawing Sheets

(56) References Cited

U.S. PATENT DOCUMENTS

| | | |
|---|---|---|
| 2005/0182009 A1 | 8/2005 | McSwiggen et al. |
| 2005/0197312 A1 | 9/2005 | Fitzgerald et al. |
| 2005/0209513 A1 | 9/2005 | Heruth et al. |

FOREIGN PATENT DOCUMENTS

| | | |
|---|---|---|
| WO | 97/42990 A1 | 11/1997 |
| WO | 98/20868 A1 | 5/1998 |
| WO | 98/47502 A1 | 10/1998 |
| WO | 02/09768 A2 | 2/2002 |
| WO | 02/38035 A2 | 5/2002 |
| WO | 02/070007 A1 | 9/2002 |
| WO | 02/074301 A1 | 9/2002 |
| WO | 02/080893 A1 | 10/2002 |
| WO | 02/085428 A2 | 10/2002 |
| WO | 02/100330 A2 | 12/2002 |
| WO | 03/026479 A2 | 4/2003 |
| WO | 03/070897 A2 | 8/2003 |
| WO | 03/070970 A2 | 8/2003 |
| WO | 03/072135 A2 | 9/2003 |
| WO | 03/083061 A2 | 10/2003 |
| WO | 2004/005551 A1 | 1/2004 |
| WO | 2004/032718 A2 | 4/2004 |
| WO | 2004/039355 A1 | 5/2004 |
| WO | 2004/066996 A1 | 8/2004 |
| WO | 2005/037323 A2 | 4/2005 |
| WO | 2005/039393 A2 | 5/2005 |
| WO | 2005/046708 A1 | 5/2005 |
| WO | 2005/059134 A1 | 6/2005 |
| WO | 2005/073164 A1 | 8/2005 |
| WO | 2005/084366 A2 | 9/2005 |

OTHER PUBLICATIONS

Yoshioka et al. J. Palliat. Care, vol. 10, 1994 Spring, pp. 10-13 (Abstract Only).*

Sakaue, et al., NF-KB Decoy Supresses Cytokine Expression and Thermal Hyperalgesia in a Rat Neuropathic Pain Model, NeuroReport, Jul. 20, 2001, pp. 2079-2084, vol. 12, Issue 10.

Lee, et al., Spinal NF-KB Activation Induces COX-2 Upregulation and Contributes to Inflammatory Pain Hypersensitivity, European Journal of Neuroscience, 2004, pp. 3375-3381, vol. 19.

Tegeder, et al., Specific Inhibition of IKB Kinases Reduces Hyperalgesia in Inflammatory and Neuropathic Pain Models in Rats, The Journal of Neuroscience, Feb. 18, 2004, pp. 1637-1645, vol. 24(7).

Nader, Nader D., et al., Clonidine Supresses Plasma and Cerebrospinal Fluid Concentrations of TNF-alpha During the Perioperative Period, Anesthesia & Analgesia, 2001, pp. 363-369, vol. 93.

Dorn, Gabriele, et al., SiRNA Relieves Chronic Neuropathic Pain, Nucleic Acids Research, 2004, pp. 1-6, vol. 32, No. 5.

Igwe, Orisa J., Modulation of Peripheral Inflammation in Sensory Ganglia by Nuclear Factor KB Decoy oligodeoxynucleotide: Involvement of SRC Kinase Pathway, Neuroscience Letters, 2005, pp. 114-119, vol. 381.

Tobinick, Edward L., e al., Perispinal TNF-alpha Inhibition for Discogenic Pain, Swiss Med. Weekly, pp. 170-177, vol. 133, 2003.

Malmberg, Annika B., et al., Antinociceptive Actions of Spinal Nonsteroidal Anti-inflammatory Agents on the Formalin Test in the Rat, The Journal of Pharmacology and Experimental Therapeutics, 1992, pp. 136-146, vol. 263.

Ryu, Bo Rum, et al., The Novel Neuroprotective Action of Sulfasalazine through Blockade of NMDA Receptors, The Journal of Pharmacology and Experimental Therapeutics, 2003, pp. 48-56, vol. 305.

Gonzalez, M. I., et al., Evaluation of Selective NK1 Receptor Antagonist CI-1021 in Animal Models of Inflammatory and Neuropathic Pain, The Journal of Pharmacology and Experimental Therapeutics, 2000, pp. 444-450, vol. 294.

Luo, Z. D., et al., Injury Type-specific Calcium Channel Alpha 2 Delta-1 Subunit Up-regulation in Rat Neuropathic Pain Models Correlates with Antiallodynic Effects of Gabapentin, The Journal of Pharmacology and Experimental Therapeutics, 2002, pp. 1199-1205, vol. 303.

Luo, Z. D., et al., Upregulation of Dorsal Root Ganglion (Alpha)2(Delta) Calcium Channel Subunit and its Correlation with Allodynia in Spinal Nerve-injured Rats, The Journal of Neuroscience, 2001, pp. 1868-1875, vol. 21.

Jett, Mary-Frances, et al., Characterization of the Analgesic and Inti-inflammatory Activities of Ketorolac and Its Enantiomers in the Rat, The Journal of Pharmacology and Experimental Therapeutics, 1999, pp. 1288-1297, vol. 288.

Milligan, E. D., et al., Spinal Glia and Proinflammatory Cytokines Mediate Mirror-image Neuropathic Pain in Rats, The Journal of Neuroscience, 2003, pp. 1026-1040, vol. 2003.

Parris, W. C. V., et al., Intrathecal Ketorolac Tromethamine Produces Analgesia after Chronic Constriction Injury of Sciatic Nerve in Rat, Canadian Journal of Anaesthesia, 1996, pp. 867-870, vol. 43.

Schafers, M., et al., Tumor Necrosis Factor-alpha induces Mechanical Allodynia after Spinal Nerve Ligation by Activation of P38 MAPK in Primary Sensory Neurons, The Journal of Neuroscience, 2003, pp. 2517-2521, vol. 23.

Sommer, c., et al., Etanercept Reduces Hyperalgesia in Experimental Painful Neuropathy, Journal of the Peripheral Nervous System, 2001, pp. 67-72, vol. 6.

Yaksh, T. L., et al., Intrathecal Ketorolac in Dogs and Rats, Toxicological Sciences, 2004, pp. 322-334, vol. 80.

Steed et al., Inactivation of TNF signalling by rationally designed dominant-negative TNF variants, Science 301:1895-98, 2003.

Jellinger and Stadelmann., Problems of cell death in neurodegeneration and Alzheimer's disease, J Alzheimer's Dis. 3:31-40, 2001.

Watterson et al., Discovery of new chemical classes of synthetic ligands that suppress neuroinflammatory responses, J Mol Neurosci 19:89-94, 2002.

Hirsch et al., The role of glial reaction and inflammation in Parkinson's Disease, Ann NY Acad Sci 991:214-28, 2003.

Ito., Anti-interleukin-6 therapy for Crohn's disease, Curr Pharm Des 9:295-305, 2003.

* cited by examiner

SYSTEMS AND METHODS TO TREAT PAIN LOCALLY

CROSS-REFERENCE TO RELATED APPLICATIONS

This application is a continuation application of U.S. patent application Ser. No. 11/460,012, filed Jul. 26, 2006, which is a continuation-in-part of U.S. patent application Ser. No. 10/972,157 filed on Oct. 22, 2004 now abandoned. The present application claims the benefit of the filing dates of the aforementioned applications and each of their disclosures is hereby incorporated by reference herein in its entirety.

FIELD OF THE INVENTION

The present invention relates to systems and methods for contributing to the local treatment of pain. More specifically, the systems and methods of the present invention contribute to the local treatment of pain by inhibiting the NFκB family of transcription factors.

BACKGROUND OF THE INVENTION

Pain can be divided into two types: acute pain and neuropathic pain. Acute pain refers to pain experienced when tissue is being damaged or is damaged. Acute pain serves at least two physiologically advantageous purposes. First, it warns of dangerous environmental stimuli (such as hot or sharp objects) by triggering reflexive responses that end contact with the dangerous stimuli. Second, if reflexive responses do not avoid dangerous environmental stimuli effectively, or tissue injury or infection otherwise results, acute pain facilitates recuperative behaviors. For example, acute pain associated with an injury or infection encourages an organism to protect the compromised area from further insult or use while the injury or infection heals. Once the dangerous environmental stimulus is removed, or the injury or infection has resolved, acute pain, having served its physiological purpose, ends.

As contrasted to acute pain, neuropathic pain serves no beneficial purpose. Neuropathic pain results when pain associated with an injury or infection continues in an area once the injury or infection has resolved. The biological basis for this type of pain that exists absent physical injury or infection baffled scientists for many years. Recently, however, evidence has mounted that neuropathic pain is caused, at least in part, by on-going (and unneeded) activation of the immune system after an injury or infection has healed. See, for example, WATKINS & MAIER (2004), PAIN, CLINICAL UPDATES, 1-4.

Local immune system activation begins when damaged cells secrete signals that recruit immune system cells to the area. One type of recruited immune system cell is the macrophage. Macrophages release interleukin-1 beta ("IL-1β"), interleukin-6 ("IL-6") and tumor necrosis factor alpha ("TNFα"), pro-inflammatory cytokines heavily involved in orchestrating the immediate and local physiological effects of injury or infection. For instance, once released, pro-inflammatory cytokines promote inflammation (swelling and redness caused by increased blood flow to the area which delivers recruited immune system cells more quickly) and also increased sensitivity to pain (by increasing the excitability and transmission of sensory nerves carrying pain information to the brain). Thus, pro-inflammatory cytokines are involved in the beneficial physiological and recuperative effects of acute pain.

Normally after an injury or infection heals, the local immune system response ceases, inflammation recedes and the increased sensitivity to pain abates. In some individuals, however, signals that terminate the immune system response are not effective entirely and pro-inflammatory cytokine activity in the area remains active. In these individuals, sensory nerves carrying pain information to the brain remain sensitized in the absence of injury or infection and the individuals can experience neuropathic pain.

Sciatica provides an example of pain that can transition from acute to neuropathic pain. Sciatica refers to pain associated with the sciatic nerve which runs from the lower part of the spinal cord (the lumbar region), down the back of the leg and to the foot. Sciatica generally begins with a herniated disc. The herniated disc itself leads to local immune system activation. The herniated disc also may damage the nerve root by pinching or compressing it, leading to additional immune system activation in the area. In most individuals, the acute pain and immune system activation associated with the injury cease once the damage has been repaired. In those individuals where immune system activation does not abate completely, however, neuropathic pain may result.

As the foregoing suggests, inhibiting the actions of pro-inflammatory cytokines can provide an effective strategy for treating acute and neuropathic pain. Inhibiting the immune system, however, is problematic as a general treatment because it leaves an individual vulnerable to infection and unable to repair tissue injuries effectively. Thus, treatments that inhibit pro-inflammatory cytokines throughout the body generally are not appropriate except in the most extreme cases of neuropathic pain. Other pain treatments likewise are not effective or appropriate for treating acute or neuropathic pain caused by pro-inflammatory cytokines. For example, narcotics do not treat pain mediated by the pro-inflammatory cytokines because narcotics block opiate receptors, a receptor type not directly involved in many effects of the pro-inflammatory cytokines. A need exists, therefore, for a locally-administered pain treatment that suppresses the actions of the pro-inflammatory cytokines.

Generally, for a protein such as a pro-inflammatory cytokine to exert an effect, the cell that will use or secrete the protein must create it. To create a protein the cell first makes a copy of the protein's gene sequence in the nucleus of the cell (this process is called transcription). Transcription factors are regulatory proteins that initiate the transcription process upon binding with DNA. Following transcription, the newly made copy of the gene sequence that encodes for the protein (called messenger RNA ("mRNA")) leaves the nucleus and is trafficked to a region of the cell containing ribosomes. Ribosomes read the sequence of the mRNA and create the protein for which it encodes. This process of new protein synthesis is known as translation. A variety of factors affect the rate and efficiency of transcription and translation. One of these factors includes the intracellular regulation of transcription factors.

The NFκB family is one group of transcription factors that plays an essential role in the inflammatory response through transcriptional regulation of a variety of genes encoding pro-inflammatory cytokines (TNFα, IL-1β, IL-6), chemokines (IL-8, MIP1α), inducible effector enzymes (iNOS and COX-2), and other molecules. Pro-inflammatory cytokines that are up-regulated by NFκB, such as TNFα and IL-1β, can also directly activate the NFκB pathway, thus establishing an autoregulatory loop that can result in chronic inflammation and pain. Activation of NFκB pathways has been shown to be important in the pathogenesis of many chronic inflammatory diseases including rheumatoid arthritis, inflammatory bowel disease, and osteoarthritis.

Thus, NFκB pathway inhibition is an attractive therapeutic strategy for the treatment of inflammatory and pain disorders. Effective NFκB pathway blockade could result in lower levels of an array of molecules including pro-inflammatory cytokines that contribute to inflammation and pain. However, because NFκB is also involved in normal cellular physiology, such as mounting an effective immune response, systemic inhibition of this pathway could result in serious side effects. For these reasons, minimizing systemic exposure of animals to NFκB inhibitory compounds is an important component of a safe therapeutic strategy.

SUMMARY OF THE INVENTION

Embodiments according to the present invention can treat pain through the local administration of one or more compounds that inhibit the NFκB pathway. Local administration of these compounds helps to prevent unwanted side effects, such as immunosuppression, associated with systemic drug administration.

Specifically, one embodiment according to the present invention is a method of treating pain comprising administering one or more NFκB inhibiting compounds locally to a patient in need thereof. In specific embodiments, the one or more NFκB inhibiting compounds are selected from the group consisting of sulfasalazine, sulindac, clonidine, helenalin, wedelolactone, pyrollidinedithiocarbamate (PDTC), Calbiochem® IKK-2 inhibitor VI, Calbiochem® IKK inhibitor III (also known as BMS-345541), and combinations thereof. The administering of the one or more NFκB inhibiting compounds can inhibit the production of one or more pro-inflammatory cytokines selected from the group consisting of interleukin-1 beta (IL-1β), tumor necrosis factor alpha (TNFα) and interleukin-6 (IL-6).

In accordance with the present invention, the one or more NFκB inhibiting compounds can be administered locally to the perispinal region of the lumbar region of a spinal cord or can be administered locally to the epidural space or the intrathecal space of the lumbar region of a spinal cord. These compounds can also be administered locally from an administration route selected from the group consisting of a catheter and drug pump, one or more local injections, polymer release, and combinations thereof.

Methods according to the present invention can be used to treat, without limitation, acute pain, neuropathic pain, sciatica and/or radicular pain.

The present invention also includes dosing regimens. In one dosing regimen according to the present invention, the dosing regimen comprises one or more NFκB inhibiting compounds and instructional information that directs the administration of the one or more NFκB inhibiting compounds for the local treatment of pain. In certain embodiments of the dosing regimens, the one or more NFκB inhibiting compounds directed to be administered are selected from the group consisting of sulfasalazine, sulindac, clonidine, helenalin, wedelolactone, pyrollidinedithiocarbamate (PDTC), Calbiochem® IKK-2 inhibitor VI, Calbiochem® IKK inhibitor III (BMS-345541), and combinations thereof.

Instructional information used in accordance with the present invention can direct the one or more NFκB inhibiting compounds to be administered locally to the perispinal region of the lumbar region of a spinal cord or to be administered locally to the epidural space or the intrathecal space of the lumbar region of a spinal cord. The instructional information can also direct the one or more NFκB inhibiting compounds to be administered locally from an administration route selected from the group consisting of a catheter and drug pump, one or more local injections, polymer release, and combinations thereof.

In another embodiment of the dosing regimens according to the present invention, the instructional information directs the one or more NFκB inhibiting compounds to be administered for the treatment of acute pain, neuropathic pain, sciatica and/or radicular pain.

In another embodiment of the dosing regimens, the dosing regimen is part of a kit used for the treatment of pain. Kits according to the present invention can include one or more of: (i) an administration form generally; (ii) an administration form comprising a catheter and drug pump, (iii) an administration form comprising one or more syringes for local injections, (iv) an administration form comprising compositions adapted for polymer release and (v) combinations thereof.

The present invention also includes compositions. In one embodiment of the compositions according to the present invention, the composition comprises one or more NFκB inhibiting compounds wherein the one or more NFκB inhibiting compounds are directed to be administered locally for the treatment of pain. In another embodiment of the compositions, the one or more NFκB inhibiting compounds are selected from the group consisting of sulfasalazine, sulindac, clonidine, helenalin, wedelolactone, pyrollidinedithiocarbamate (PDTC), Calbiochem IKK-2 inhibitor VI, Calbiochem IKK inhibitor III (BMS-345541) and combinations thereof.

Compositions according to the present invention can be directed to be administered locally to the perispinal region of the lumbar region of a spinal cord or can be directed to be administered locally to the epidural space or the intrathecal space of the lumbar region of a spinal cord. The compositions can also be directed to be administered locally from an administration route selected from the group consisting of a catheter and drug pump, one or more local injections, polymer release and combinations thereof.

DETAILED DESCRIPTION

Figure 1:
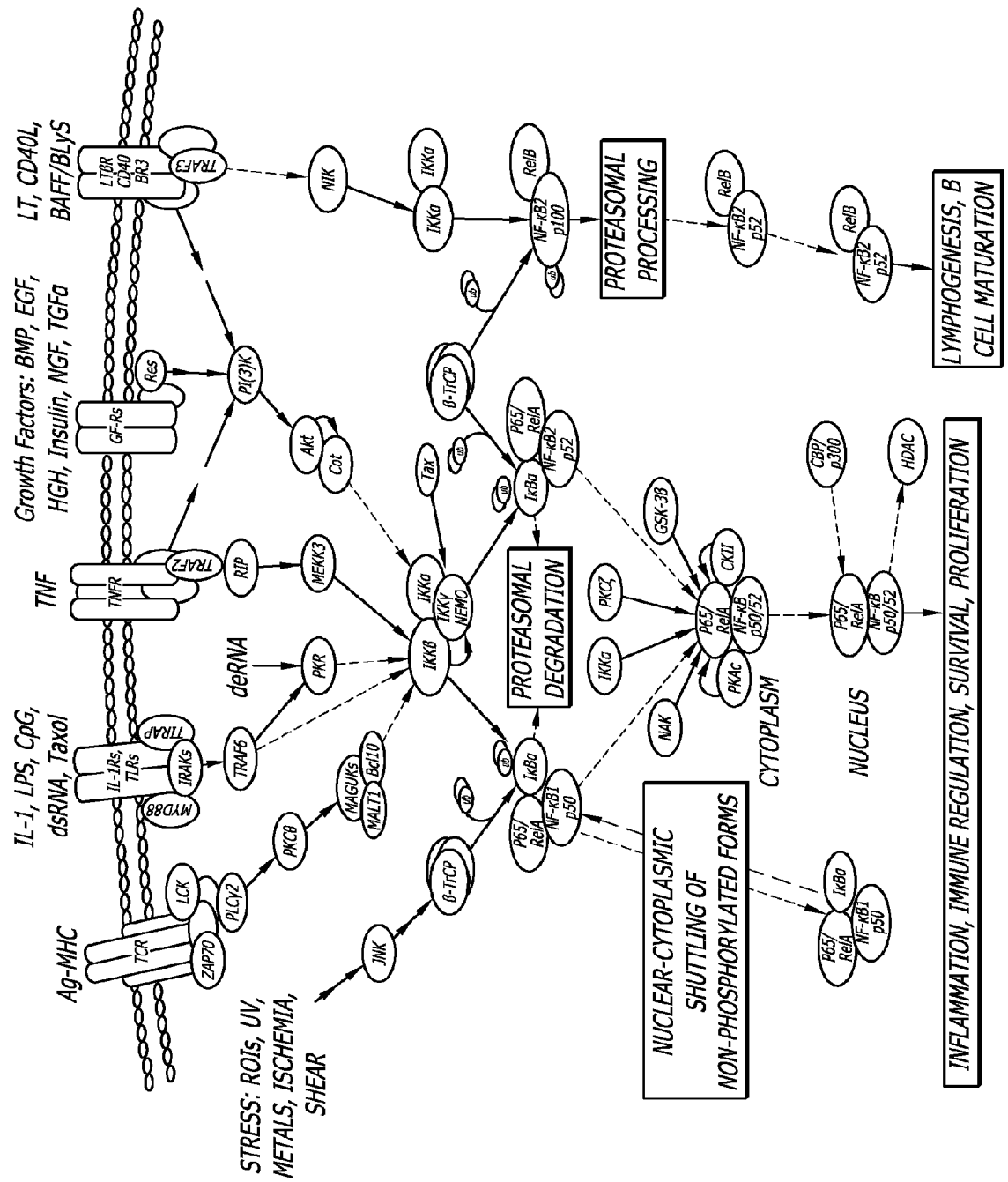
FIG. 1 depicts a schematic representation of the NFκB activation pathway.

While the sensation of pain can serve beneficial purposes, in many instances, such as neuropathic pain (which occurs in the absence of injury or infection) it does not and is highly undesirable. Problematic pain requiring treatment is believed to be caused at least in part due to local immune activation. The local immune activation is mediated largely by pro-inflammatory cytokines including interleukin-1 beta ("IL-1β"), tumor necrosis factor alpha ("TNFα") and interleukin-6

("IL-6"). Sciatica provides one non-limiting example of pain that can be caused by local pro-inflammatory cytokine activity.

As the foregoing suggests, inhibiting the actions of pro-inflammatory cytokines can provide an effective strategy for treating pain. Inhibiting the immune system, however, is problematic as a general treatment because it leaves an individual vulnerable to infection and unable to repair tissue injuries effectively. Thus, treatments that systemically inhibit pro-inflammatory cytokines throughout the body are not appropriate except in the most extreme cases.

For a protein such as a pro-inflammatory cytokine to exert an effect, the cell that will use or secrete the protein must create it. Thus, one avenue to inhibit the local actions of pro-inflammatory cytokines is to inhibit intracellular mechanisms that lead to their production and release. The NFκB family is the primary group of transcription factors that plays an essential role in regulating the transcription of genes encoding pro-inflammatory cytokines (TNFα, IL-1β, IL-6), chemokines (IL-8, MIP1α), inducible effector enzymes (iNOS and COX-2), and other molecules. Thus, NFκB pathway inhibition is one attractive therapeutic strategy for the treatment of inflammatory and pain disorders. Effective NFκB pathway blockade can result in lower levels of an array of molecules including pro-inflammatory cytokines that contribute to inflammation and pain. However, because NFκB is also involved in normal cellular physiology such as mounting an effective immune response, systemic inhibition of the pathway may result in serious side effects. For example global inhibition of the NFκB pathway in adult animals can render them susceptible to opportunistic infections. Further, gene targeting studies in mice have shown that complete inactivation of nearly any member of the NFκB pathway (at least during development) results in significant immune system defects and/or embryonic lethality. For these reasons, minimizing systemic exposure of animals to NFκB inhibitory compounds is an important component to a safe therapeutic strategy for the treatment of pain.

The NFκB transcription factor family represents a group of structurally related and evolutionarily conserved proteins that includes five members in mammals: Rel (c-Rel), RelA (p65), RelB, NFκB1 (p50), and NFκB2 (p52). These molecules form functional transcription factors by complexing into hetero- or homodimers of the NFκB/Rel protein subunits. The most prevalent form of NFκB is a heterodimer of the p65 and p50 subunits.

NFκB pathway activation (see FIG. 1) is regulated through a series of events. In unstimulated cells, NFκB is sequestered in the cytoplasm in an inactive form, bound to regulatory proteins called inhibitors of κB (IκB). A variety of stimuli including pro-inflammatory cytokines such as TNFα and IL-1β induce the phosphorylation of the IκB proteins (IκBα and IκBβ) at specific $NH_2$-terminal serine residues. The phosphorylated IκB proteins quickly become ubiquinated and degraded by the proteasome. The released NFκB proteins are then able to translocate to the cell nucleus and induce the transcription of a variety of genes containing their cognate DNA binding recognition sequences.

A key step in NFκB activation described in the preceding paragraph is the phosphorylation of the IκB proteins. This phosphorylation event is mediated by a specific protein complex known as IκB kinase (IKK). IKK is composed of two catalytic subunits IKKα and IKKβ, and a regulatory subunit named NFκB essential modulator (NEMO) or IKKγ. Cells deficient in either IKKα or IKKβ retain some inducible NFκB activity suggesting their distinct roles in NFκB pathway activation. Conversely, in cells lacking IKKγ, NFκB activation is completely blocked upon the induction of a variety of stimuli (including TNFα, IL-1, and lipopolysaccharide (LPS) exposure).

Regarding the use of NFκB inhibitors to treat pain, endoneural injections of an NFκB transcription factor decoy (at the site of peripheral injury) have been shown to significantly reduce thermal hyperalgesia in a rat model of neuropathic pain. In this model NFκB inhibition also results in lower levels of a variety of pro-inflammatory mediators (including TNFα, IL-1β, IL-6, IFN-γ, and iNOS). Sakaue et al., (*Neuroreport.* 2001, 12(10):2079). Spinal administration of NFκB inhibitors (ODN decoys and pyrrolidine dithiocarbamate (PDTC)) have also been shown to significantly reduce mechanical allodynia and thermal hyperalgesia in the Complete Freund's Adjuvant (CFA) inflammatory pain model. Lee et al., (*Euro J. Neurosci.* 2004, 19:3375). Further, Tegeder et al., (*J. Neurosci.* 2004, 24(7):1637) have reported that a specific IKK-13 inhibitor (S1627) reduces hyperalgesia in inflammatory and neuropathic pain models (zymosan-induced paw inflammation) in rats. In addition, this inhibitor also reduces tactile allodynia in the chronic constriction injury model (CCl) of neuropathic pain. These studies demonstrate the efficacy of NFκB pathway blockade in the treatment of inflammatory and neuropathic pain.

Co-pending application publication number US2005/0095246A1 ("the '246 application") to which this application claims priority and which is incorporated by reference fully herein describes techniques to treat neurological disorders by attenuating the production of pro-inflammatory mediators. The '246 application describes the use of devices such as pumps/catheters and polymer-based drug depots for the local (peripheral, intrathecal, intraparenchymal) delivery of inhibitors of pro-inflammatory mediators (including members of the NFκB pathway; IKK-α, β, and γ) to treat inflammatory disorders. Embodiments described in the present application stem from these initial disclosures and also provide novel compounds to locally inhibit NFκB in the local treatment of pain through the local administration of these compounds.

EXAMPLES

The behavioral animal model of chronic constriction injury ("CCl") was chosen to evaluate the efficacy of NFκB inhibitors as a pain treatment. This model may mimic pain associated with sciatica in humans. To induce CCl, each animal was anesthetized by intraperitoneal ("i.p.") injection of sodium pentobarbital at a dose of 60 mg/kg body weight. The animal's right common sciatic nerve was exposed and freed from adherent tissue at mid-thigh by separating the muscle (biceps femoris) by blunt dissection. Four loose ligatures were placed 1 mm apart, using chromic gut (4-0 absorbable suture, Jorgensen Laboratories Inc., Loveland, Colo.).

Example 1

Animals were randomly assigned to treatment groups and administered control or test compounds as follows: animals received either vehicle (Phosphate Buffered Saline; PBS), the protein-based TNFα inhibitor, Enbrel® as a positive control (3 mg/kg Immunex Corp., Seattle, Wash.) or sulfasalazine, a small molecule inhibitor of NFκB at a dose of 5 mg/kg or 50 mg/kg.

Animal behavioral testing was conducted on Days 7, 14 and 21 after CCl. In the thermal hyperalgesia test, animals were placed in the clear plastic chamber of a plantar analgesia instrument and allowed to acclimate to the environment for 15 minutes. After the acclimation period, a radiant (heat) beam source stimulus was applied to the CCl hind paw of each animal. The heat source device was set at an intensity of 50, and a maximum latency period of 15 seconds was set to prevent tissue damage according to the recommendations of the instrument manufacturer. If a paw withdrawal occurred within the 15 second period, an automated control interrupted both the stimulus and timer, turning off the radiant beam and recording the latency of time to paw withdrawal. Data was analyzed using a one-way analysis of variance at each test day.

Figures 2, 3:
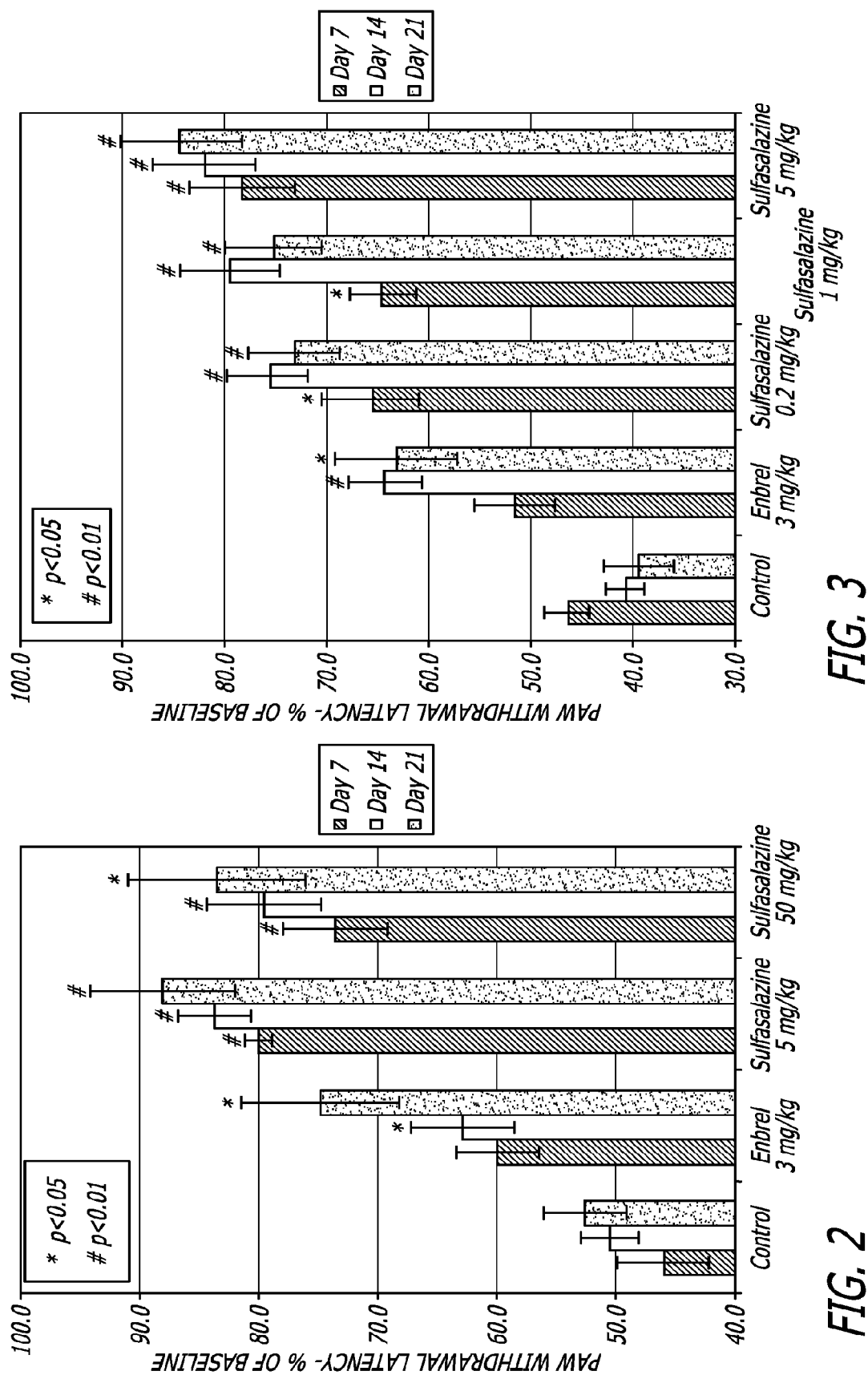
FIGS. 2 and 3 show the effect of the NFκB inhibitor sulfasalazine on pain sensitivity as measured by paw withdrawal latencies.

FIG. 2 demonstrates that the protein-based pro-inflammatory cytokine inhibitor Enbrel® is effective to inhibit pain associated with CCl on all test days. NFκB inhibitors, however, were more effective at inhibiting pain associated with CCl on all test days. Specifically, animals that received vehicle showed mean paw withdrawal latencies of about 45%, 50% and 53% over baseline on test days 7, 14 and 21 respectively. Animals that received Enbrel® showed mean paw withdrawal latencies of about 60%, 63% and 75% over baseline on test days 7, 14 and 21 respectively. Animals receiving 5 mg/kg sulfasalazine showed mean paw withdrawal latencies of about 80%, 83% and 87% over baseline while those receiving 50 mg/kg showed mean paw withdrawal latencies of about 74%, 79% and 83% over baseline on test days 7, 14 and 21 respectively. This data demonstrates that NFκB inhibition can provide an effective mechanism to decrease pain sensitivity.

Example 2

In a subsequent study, additional lower doses of sulfasalazine were evaluated for their effectiveness as a pain treatment using the CCl model. Specifically, the same methods as described above were used except that sulfasalazine was administered at doses of 5 mg/kg; 1 mg/kg or 0.2 mg/kg. As can be seen in FIG. 3, control animals receiving vehicle showed paw withdrawal latencies averaging an increase of about 45%, 41% and 39% over baseline on test days 7, 14 and 21 respectively. Positive control animals receiving the protein-based TNFα inhibitor, Enbrel® increased paw withdrawal latencies to about 51%, 63% and 62% over baseline on test days 7, 14 and 21 respectively. Again, however, all doses of sulfasalazine increased paw withdrawal latencies on all test days even further (to an average of between about 65% to about 85% over baseline measures on all test days), again suggesting that sulfasalazine and NFκB inhibition can provide an effective pain treatment. Indeed, this data suggests that sulfasalazine can provide a more effective pain treatment than protein-based inhibitors such as Enbrel®.

Example 3

Figure 4:
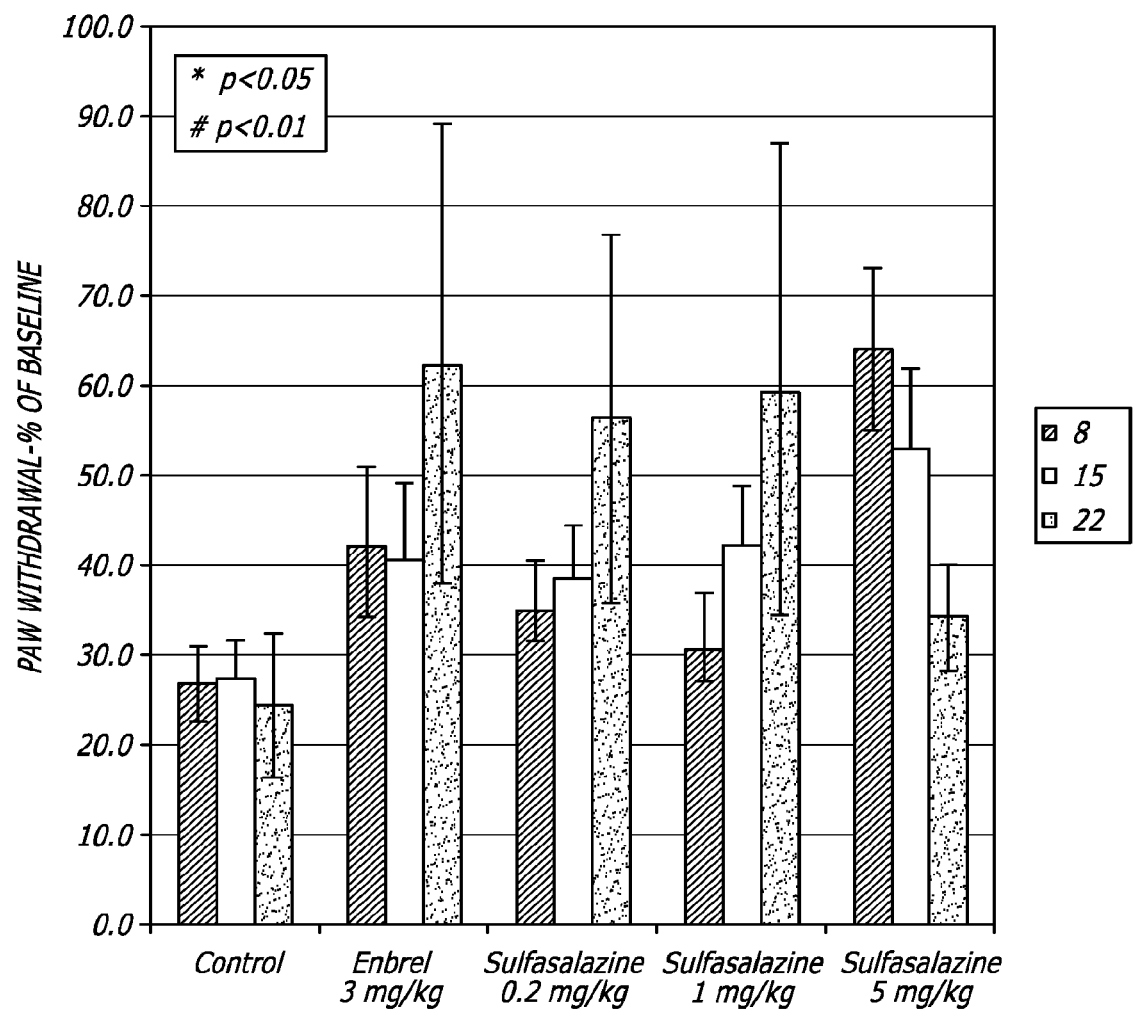
FIG. 4 shows the effect of the NFκB inhibitor sulfasalazine on pain sensitivity as measured in a mechanical allodynia paradigm.

The ability of sulfasalazine to inhibit pain was also evaluated using a different sensitivity measure following CCl, namely mechanical (or tactile) allodynia. In this study, mechanical allodynia was determined in reaction to probing with von Frey filaments (Stoelting, Wood Dale, Ill.). Mechanical sensitivity was measured on Days 8, 15 and 22 following CCl by determining the median 50% foot withdrawal threshold for von Frey filaments using the up-down method described in Chaplan et al. (*J Neurosci Methods* 1994; 54:55) which is incorporated by reference herein for its teachings regarding the up-down method. Rats were placed under a plastic cover (9×9×20 cm) on a metal mesh floor. The area tested was the middle glabrous area between the footpads of the plantar surface of the injured hind paw within the L4 innervation area. The plantar area was touched with a series of 9 von Frey hairs with approximately exponentially incremental bending forces (von Frey values: 3.61, 3.8, 4.0, 4.2, 4.41, 4.6, 4.8, 5.0, and 5.2; equivalent to: 0.41, 0.63, 1.0, 1.58, 2.51, 4.07, 6.31, 10, and 15.8 g). The von Frey hair was presented perpendicular to the plantar surface with sufficient force to cause slight bending and held for approximately 3 to 4 seconds. Abrupt withdrawal of the foot (paw flinching) was recorded as a response. Any rat showing a mechanical threshold of more than 3.24 g was eliminated from the study. As can be seen in FIG. 4, Enbrel® and sulfasalazine both decreased sensitivity in this paradigm when compared to controls, further suggesting that sulfasalazine and NFκB inhibition can provide an effective pain treatment when administered at appropriate dosages.

Example 4

Figure 5A:
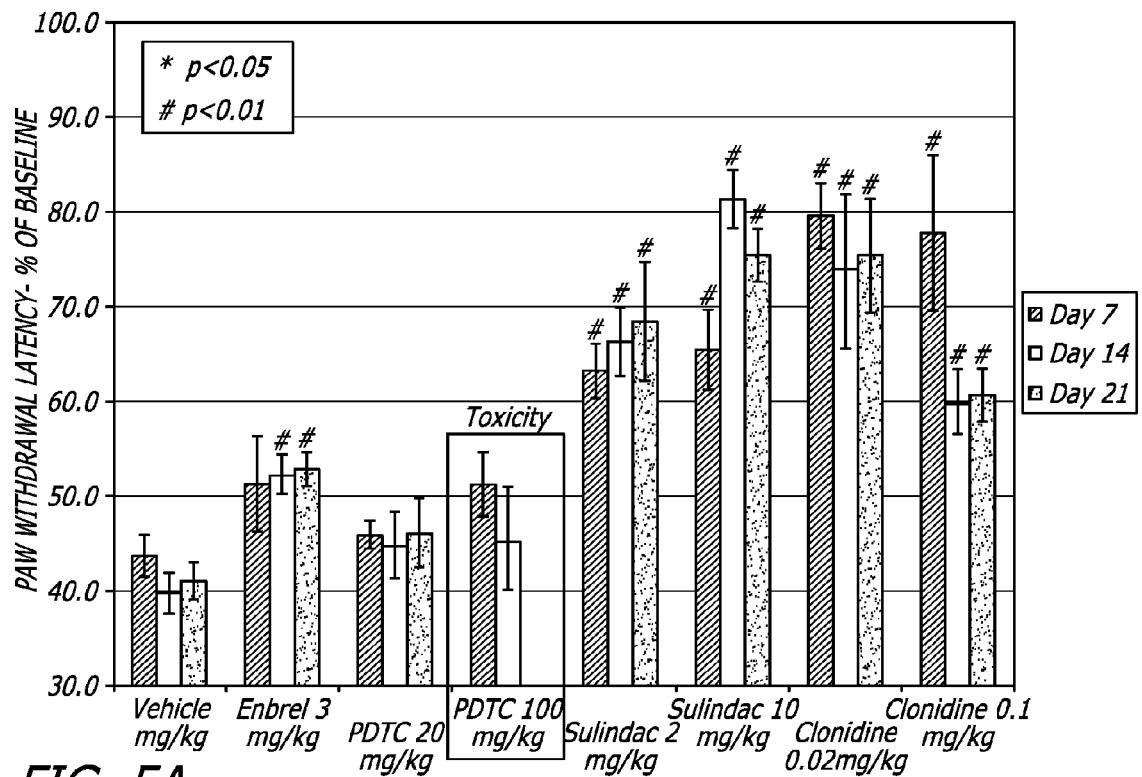
FIGS. 5A-5B show the effect of additional NFκB inhibitors on pain sensitivity measured by paw withdrawal latencies and in a mechanical allodynia paradigm.

Next, the ability of other NFκB inhibitors to decrease pain sensitivity in the paw withdrawal and mechanical allodynia paradigms following CCl were evaluated. In this study, the previously described methods for CCl, paw withdrawal and mechanical allodynia testing were followed except that animals received vehicle control; 3 mg/kg Enbrel® as a positive control; 20 mg/kg or 100 mg/kg pyrollidinedithiocarbamate (PDTC); 2 mg/kg or 10 mg/kg sulindac; or 0.02 mg/kg or 0.1 mg/kg clonidine. As can be seen in FIG. 5A, vehicle controls showed average paw withdrawal latencies of about 41% over baseline on all three test days. Positive control animals receiving Enbrel® increased paw withdrawal latencies to an average of about 51% over baseline on all three test days. Animals receiving 2 mg/kg sulindac increased latencies to about 65% over baseline on all three test days while those receiving 10 mg/kg increased latencies to about 65%, 81% and 75% over baseline on test days 7, 41 and 21 respectively. Animals receiving 0.02 mg/kg clonidine showed an increase in paw withdrawal latencies over baseline of about 75%-79% on all three test days and those receiving 0.1 mg/kg clonidine showed an increase of about 78%, 60% and 61% over baseline on test days 7, 41 and 21 respectively. This data suggests that NFκB inhibitors reduce pain sensitivity further suggesting that NFκB inhibition can provide an effective pain treatment. Interestingly, in this study, while PDTC did increase paw withdrawal latencies over control levels, this compound was not as effective at reducing pain sensitivity as other NFκB inhibiting compounds. This result could be a function of dose or administration route. Indeed, animals receiving 100 mg/kg PDTC were removed from the study following the second day of testing due to drug toxicity.

Figure 5B:
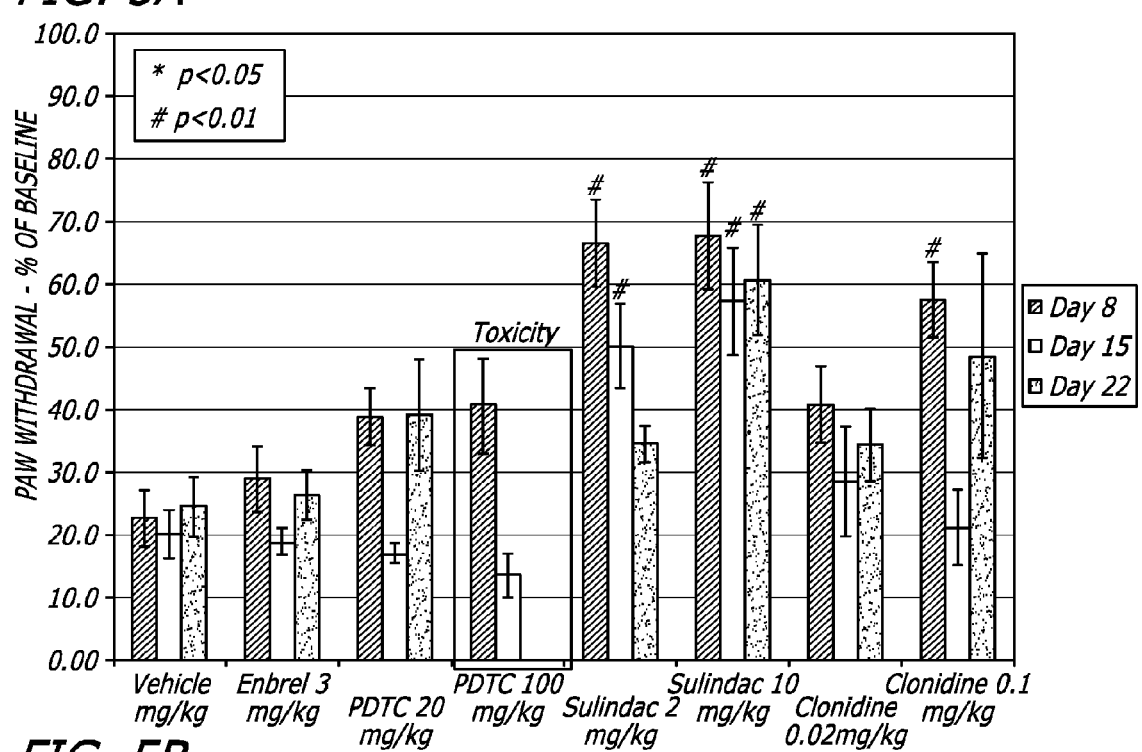

In the mechanical allodynia test, as can be seen in FIG. 5B, all NFκB inhibitors, (with the potential exception of PDTC), decreased pain sensitivity when compared to control animals receiving vehicle or Enbrel®. Both doses of sulindac and the higher dose (0.1 mg/kg) of clonidine most significantly decreased pain sensitivity. These compounds decreased pain sensitivity on days 8, 15 and 22 respectively as follows: sulindac (2 mg/kg): about 66%, 50% and 35%; sulindac (10 mg/kg): about 68%, 58% and 60%; clonidine (0.1 mg/kg): about 58%, 20% and 48%. Animals receiving vehicle or Enbrel® showed increases between about 19% and 25%. Again, while PDTC showed some effect in decreasing pain sensitivity, the effect was not as strong as that seen with sulindac or clonidine. Further, while the low dose of clonidine decreased sensitivity, it did not show as strong an effect in the mechanical allodynia test. This result may indicate that the higher dose of clonidine is a more appropriate dose for its use in the treatment of pain.

Example 5

Figure 6:
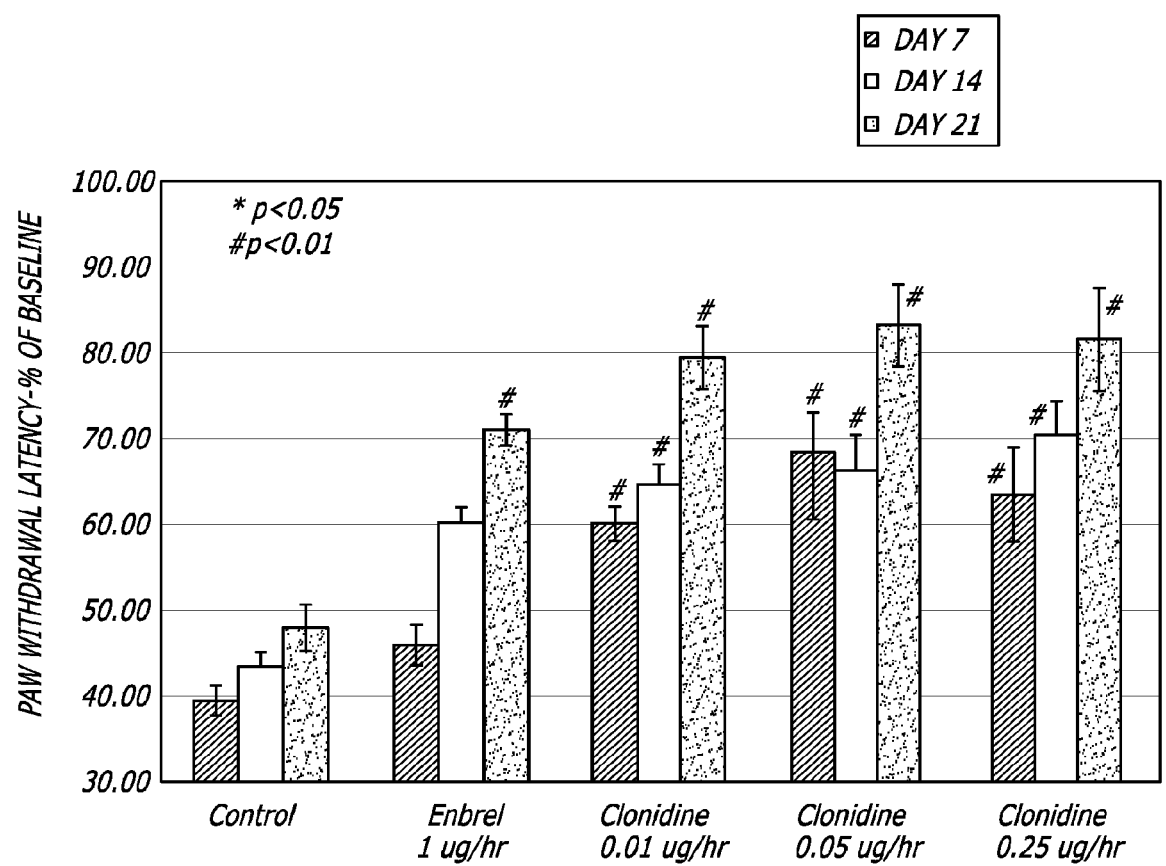
FIG. 6 shows the effect of the NFκB inhibitor clonidine on pain sensitivity as measured by paw withdrawal latencies.

Following the previous experiment, the effect of local doses of clonidine on pain sensitivity was explored. Animals were administered vehicle or test substances through a subcutaneously implanted Alzet pump. Again, the previously described methods for CCI and paw withdrawal latency measurements were followed except that in the presently described experiment animals received either vehicle control; 1 µg/hour Enbrel® as a positive control; 0.01 µg/hour clonidine; 0.05 µg/hour clonidine; or 0.25 µg/hour clonidine. As can be seen in FIG. 6, vehicle controls showed average paw withdrawal latencies of about 39%, 43% and 47% over baseline on test days 7, 14 and 21 respectively. Animals receiving Enbrel® showed paw withdrawal latencies of about 45%, 60% and 71% over baseline on test days 7, 14 and 21 respectively. Animals receiving 0.01 µg/hour clonidine showed paw withdrawal latencies of about 60%, 64% and 79% over baseline on test days 7, 14 and 21 respectively. Animals receiving 0.05 µg/hour clonidine showed paw withdrawal latencies of about 68%, 64% and 83% over baseline on test days 7, 14 and 21 respectively. Animals receiving 0.25 µg/hour clonidine showed paw withdrawal latencies of about 63%, 70% and 82% over baseline on test days 7, 14 and 21 respectively. In this study, all doses of clonidine caused significant increases in paw withdrawal latencies on all three test days. Therefore, these results further suggest that clonidine can provide an effective pain treatment when administered locally. Dosing of compounds such as clonidine can substantially reduce the systemic exposure of the drug without compromising the efficacy of treatment. In the example given, there was a 25 fold dose reduction without loss of efficacy.

The disclosed invention describes the use of a therapeutic agent to block activation of the NFκB signaling pathway to alleviate pain. Pain is likely reduced by these inhibitors through their effect in reducing levels of pro-inflammatory cytokines and other molecules involved in the inflammation response. The therapeutic agent may be a small molecule inhibitor of NFκB pathway activation or other effective NFκB inhibitors. Non-limiting examples of potential therapeutic agents for use in accordance with the present invention can include anti-oxidants that have been shown to inhibit NFκB, proteasome and protease inhibitors that inhibit NFκB, and IκBa phosphorylation and/or degradation inhibitors. Examples of such compounds include, without limitation, α-lipoic acid, α-tocopherol, allicin, 2-amino-1-methyl-6-phenylimidazo[4,5-]pyridine, anetholdithiolthione, apocynin, 5,6,3',5'-tetramethoxy 7,4'-hydroxyflavone, astaxanthin, benidipine, bis-eugenol, *bruguiera gymnorrhiza* compounds, butylated hydroxyanisole, cepharanthine, caffeic acid phenethyl ester, carnosol, β-carotene, carvedilol, catechol derivatives, chlorogenic acid, cocoa polyphenols, curcumin, dehydroepiandrosterone and dehydroepiandrosterone sulfate, dibenzylbutyrolactone lignans, diethyldithiocarbamate, diferoxamine, dihydroisoeugenol, dihydrolipoic acid, dilazep+ fenofibric acid, dimethyldithiocarbamates, dimethylsulfoxide, disulfuram, ebselen, edaravone, epc-k1, epigallocatechin-3-gallate, ergothioneine, ethylene glycol tetraacetic acid, flavonoids (crataegus; *boerhaavia diffusa* root; xanthohumol), .gamma.-glutamylcysteine synthetase, *ganoderma lucidum* polysaccharides, garcinol, *ginkgo biloba* extract, hematein, 23-hydroxyursolic acid, iron tetrakis, isovitexin, kangen-karyu extract, 1-cysteine, lacidipine, lazaroids, lupeol, magnolol, maltol, manganese superoxide dismutase, extract of the stem bark of *mangifera indica* I, melatonin, mulberry anthocyanins, n-acetyl-1 cysteine, nacyselyn, nordihydroguaiaritic acid, ochnaflavone, orthophenanthroline, hydroquinone, tert-butyl hydroquinone, phenylarsine oxide, *phyllanthus urinaria*, pyrrolinedithiocarbamate, quercetin (low concentrations), redox factor I, rotenone, roxithromycin, s-allyl-cysteine, sauchinone, spironolactone, strawberry extracts, taxifolin, tempol, tepoxaline, vitamin C, vitamin B6, vitamin E derivatives, α-torphryl succinate, α-torphryl acetate, 2,2,5,7,8-pentamethyl-6-hydroxychromane, yakuchinone α and β, n-acetyl-leucinyl-leucynil-norleucynal, n-acetyl-leucinyl-leucynil-methional, carbobenzoxyl-leucinyl-leucynil-norvalinal, carbobenzoxyl-leucinyl-leucynil-leucynal, lactacystine, β-lactone, boronic acid peptide, ubiquitin ligase inhibitors, bortezomib, salinosporamide α, cyclosporin α, tacrolimus, deoxyspergualin, 15 deoxyspergualin, analogs of 15-deoxyspergualin, n-acetyl-dl-phenylalanine-β-naphthylester, n-benzoyl 1-tyrosine-ethylester, 3,4-dichloroisocoumarin, diisopropyl fluorophosphate, n-α-tosyl-1-phenylalanine chloromethyl ketone, n-α-tosyl-1-lysine chloromethyl ketone, desloratadine, salmeterol, fluticasone propionate, protein-bound polysaccharide from basidiomycetes, calagualine, golli bg21, npm-alk oncoprotein, ly29, ly30, ly294002, evodiamine, rituximab, kinase suppressor of ras, pefabloc, rocaglamides, betaine, tnap, geldanamycin, grape seed proanthocyanidins, pomegranate fruit extract, tetrandine, 4(2'-aminoethyl) amino-1,8-dimethylimidazo(1,2-α)quinoxaline, 2-amino-3-cyano-4-aryl-6-(2-hydroxy-phenyl)pyridine derivatives, acrolein, anandamide, as602868, cobrotoxin, dihydroxyphenylethanol, herbimycin α, inhibitor 22, isorhapontigenin, manumycin α, mlb120, nitric oxide, nitric oxide donating aspirin, thienopyridine, acetyl-boswellic acids, β-carboline, cyl-19s, cyl-26z, synthetic α-methylene-γ-butyrolactone derivatives, 2-amino-6-[2-(cyclopropylmethoxy)-6-hydroxyphenyl]-4-piperidin-4-ylnicotinonitrile, plant compound α, flavopiridol, cyclopentones, jesterone dimmer, ps-1145, 2-[(aminocarbonyl)amino]-5-acetylenyl-3-thiophenecarboxamides, 1' acetoxychavicol acetate, apigenin, cardamomin, synthetic triterpenoid, chs 828 (anticancer drug), diosgenin, furonaphthoquinone, guggulsterone, heparin-binding epidermal growth factor-like growth factor, falcarindol, hepatocyte growth factor, honokiol, hypoestoxide, γ-mangostin, garcinone-β, kahweol, kava derivatives, ml120b, mx781 (retinoid antagonist), n-acetylcysteine, nitrosylcobalamin (vitamin B12 analog), non-steroidal anti-inflammatory drugs (NSAIDs), hepatits c virus ns5b, pan1 (aka nalp2 or pypaf2), n-(4-hydroxyphenyl)retinamide, sulforaphane, phenylisothiocyanate, survanta, piceatannol, 5-hydroxy-2-methyl-1,4-naphthoquinone, pten (tumor suppressor), theaflavin, tilianin, zerumbone, silibinin, sulfasalazine, sulfasalazine analogs, rosmarinic acid, staurosporine, γ tocotrienol, wedelolactone, betulinic acid, ursolic acid, thalidomide, interleukin-10, mollusum contagiosum virus mc159 protein, monochloramine, glycine chloramine, anethole, anti-thrombin III, *artemisia vestita*, aspirin, sodium salicylate, azidothymidine, baoganning, e3((4-methylphenyl)-sulfonyl)-2-propenenitrile, e3((4-t-butylphenyl)-sulfonyl)-2-propenenitrile, benzyl isothiocyanate, cyanidin 3-o-glucoside, cyanidin 3-o-(2(g)-xylosylrutinoside, cyanidin 3-o-rutinoside, buddlejasaponin IV, cacospongionolide β, carbon monoxide, carboplatin, cardamonin, chorionic gonadotropin, cycloepoxydon, 1-hydroxy-2-hydroxymethyl-3-pent-1-enylbenzene, decursin, dexanabinol, digitoxin, diterpenes (synthetic), docosahexaenoic acid, extensively oxidized low density lipoprotein, 4-hydroxynonenal, fragile histidine triad protein, gabexate mesilate, [6]-gingerol, casparol, imatanib, *glossogyne tenuifolia*, ibuprofen, indirubin-3'-oxime, interferon-α, licorice extracts, methotrexate, nafamostat mesilate, oleandrin, omega 3 fatty acids, panduratin α, petrosaspongiolide m, pinosylvin, *plagius flosculosus* extract polyacetylene spiroketal, phytic acid, prostaglandin α1, 20(s)-protopanaxatriol, rengyolone, rottlerin, saikosaponin-d, saline (low Na$^+$ isotonic), *salvia miltiorrhizae* water-soluble extract, pseudochelerythrine, 13-methyl-[1,3]-benzodioxolo-[5,6-c]-1,3-dioxolo-4,5 phenanthridinium), scoparone, silymarin, socs1, statins, sulindac, thi 52 (1-naphthylethyl-6,7-dihydroxy-1,2,3,4-tetrahydroisoquinoline), 1,2,4-thiadiazolidine derivatives, vesnarinone, xanthoangelol d, yc-1, yopj, acetaminophen, activated protein c, alachlor, α-melanocyte-stimulating hormone, amentoflavone, *artemisia capillaris* thunb extract, *artemisia iwayomogi* extract, 1-ascorbic acid, antrodia camphorate, aucubin, baicalein, β-lapachone, blackberry extract, buchangtang, capsaicin, catalposide, core protein of hepatitis c virus, cyclolinteinone, diamide, dihydroarteanniun, dobutamine, e-73 (cycloheximide analog), ecabet sodium, emodin, ephedrae herba, equol, erbstatin, estrogen, ethacrynic acid, fosfomycin, fungal gliotoxin, gamisanghyulyunbueum, genistein, genipin, glabridin, glimepiride, glucosamine sulfate, glutamine, gumiganghwaltang, heat shock protein-70, hypochlorite, interleukin-13, isomallotochromanol, isomallotochromene, vaccinia virus protein, *kochia scoparia* fruit, leflunomide metabolite, losartin, 5'-methylthioadenosine, momordin I, *morinda officinalis* extract, murr1 gene product, neurofibromatosis-2 protein, u0126, penetratin, pervanadate, β-phenylethyl and 8-methylsulphinyloctyl isothiocyanates, phenyloin, platycodin saponins, polymyxin β, *poncirus trifoliata* fruit extract, probiotics, pituitary adenylate cyclase-activating polypeptide, prostaglandin 15-deoxy-delta(12, 14)-pgj(2), resiniferatoxin, sabaeksan, *saccharomyces boulardii* anti-inflammatory factor, sesquiterpene lactones (parthenolide; ergolide; guaianolides), st2 (interleukin-1-like receptor secreted form), thiopental, tipifarnib, titanium, tnp-470, stinging nettle (*urtica dioica*) plant extracts, *trichomomas vaginalis* infection, triglyceride-rich lipoproteins, ursodeoxycholic acid, *xanthium strumarium* I, vasoactive intestinal peptide, HIV-1 vpu protein, epoxyquinone a monomer, ro106-9920, conophylline, mol 294, perrilyl alcohol, mast205, rhein, 15-deoxy-prostaglandin j(2), *antrodia camphorata* extract, β-amyloid protein, surfactant protein α, dq 65-79 (aa 65-79 of the α helix of the -chain of the class II HLA molecule dqa03011), c5a, glucocorticoids (dexamethasone, prednisone, methylprednisolone), interleukin-10, interleukin-11, α-pinene, vitamin D, fox1j, dioxin, *agastache rugosa* leaf extract, alginic acid, astragaloside iv, atorvastatin, blue honeysuckle extract, n(1)-benzyl-4-methylbenzene-1,2-diamine, *buthus martensi* karsch extract, canine distemper virus protein, carbaryl, celastrol, chiisanoside, dehydroxymethylepoxyquinomicin, dipyridamole, diltiazem, eriocalyxin β, estrogen enhanced transcript, gangliosides, glucorticoid-induced leucine zipper protein, *harpagophytum procumbens* extracts, heat shock protein 72, hirsutenone, indole-3-carbinol, jm34 (benzamide derivative), 6-hydroxy-7-methoxychroman-2-carboxylic acid phenylamide, leptomycin β, levamisole, 2-(4-morpholynl) ethyl butyrate hydrochloride, nls cell permeable peptides, 2',8"-biapigenin, nucling, o,o'-bismyristoyl thiamine disulfide, oregonin, 1,2,3,4,6-penta-o-galloyl-β-d-glucose, *platycodi radix* extract, phallacidin, piperine, pitavastatin, pn-50, rela peptides (p1 and p6), retinoic acid receptor-related orphan receptor-α, rhubarb aqueous extract, rolipram, *salvia miltiorrhoza* bunge extract, sc236 (a selective cox-2 inhibitor), selenomethionine, *sophorae radix* extract, sopoongsan, sphondin, younggaechulgam-tang, zud protein, zas3 protein, clarithromycin, fluvastatin, leflunomide, oxidized 1-palmitoyl-2-arachidonoyl-sn-glycero-3-phosphorylcholine, serratamolide, moxifloxacin, *sorbus commixta* cortex, cantharidin, *cornus officinalis* extract, neomycin, omapatrilat, enalapril, cgs 25462, onconase, paeoniflorin, rapamycin, *sargassum hemiphyllum* methanol extract, shenfu, tripterygium polyglycosides, triflusal, hepatoma protein, andrographolide, melittin, 1'-acetoxychavicol acetate, 2-acetylaminofluorene, actinodaphine, adiponectin, nicotinamide, 3-aminobenzamide, 7-amino-4-methylcoumarin, aminone, angiopoietin-1, anthocyanins, sequiterpene lactones, artemisinin, atrial natriuretic peptide, atrovastat, avra protein, baicalein, benfotiamine, catenin, biliverdin, bisphenol α, bovine serum albumin, brazilian, bromelain, calcium/calmodulin-dependent kinase kinase, calcitriol, camptothecin, *sutherlandia frutescens*, caprofin, capsiate, carbocisteine, cat's claw bark, maca, celecoxib, germcitabine, cheongyeolsaseuptang, chitosan, ciclosporin, cinnamaldehyde, 2-methoxycinnamaldehyde, 2-hydroxycinnamaldehyde, guaianolide 8-deoxylactucin, chlorophyllin, chondrotin sulfate proteoglycan degradation product, clarithromycin, cloricromene, commerical peritoneal dialysis solution, compound K, 6-hydroxy-7-methoxychroman-2-carboxylic acid phenylamide, cryptotanshinone, cyanoguanidine, cytochalasin d, da-9201 (from black rice), danshenshu, decoy oligonucleotides, diarylheptanoid 7-(4'-hydroxy-3'-methoxyphenyl)-1-phenylhept-4-en-3-one, α-difluoromethylornithine, dim/13c, diterpenoids from *isodon rubescens* or liverwort jungermannia, 4,10-dichloropyrido[5,6:4,5]thieno[3,2-d':3,2-d]-1,2,3-ditriazine, e3330, ent-kaurane diterpenoids, epinastine hydrochloride, epoxyquinol α, erythromycin, evans blue, fenoldopam, fexofenadine hydrochloride, fibrates, fk778, flunixin meglumine, flurbiprofen, *fomes fomentarius* methanol extracts, fucoidan, glycoprotein-120, gallic acid, *ganoderma lucidum*, homeobox protein, geranylgeraniol, ghrelin, ginkgolide glycyrrhizin, halofuginone, helenalin, herbal compound 861, HIV-1 resistance factor, hydroxyethyl starch, hydroxyethylpuerarin, hypercapnic acidosis, hypericin, interleukin 4, IKB-like proteins, imd-0354, insulin-like growth factor binding protein-3,jsh-21 (n1-benzyl-4-methylbenzene-1,2-diamine), kamebakaurin, kaposi's sarcoma-associated herpesvirus k1 protein, ketamine, kt-90 (morphine synthetic derivative), linoleic acid, lithospermi radix, lovastatin, macrolide antibiotics, mercaptopyrazine, 2-methoxyestradiol, 6 (methylsulfinyl)hexyl isothiocyanate, metals (chromium, cadmium, gold, lead, mercury, zinc, arsenic), mevinolin, monomethylfumarate, moxifloxacin, myricetin, myxoma virus mnf, ndpp1, n-ethyl-maleimide, naringen, nicorandil, nicotine, nilvadipine, nitrosoglutathione, extracts of ochna macrocalyx bark, leucine-rich effector proteins of *salmonella & shigella*, omega-3 fatty acids oridonin 1,2,3,4,6-penta-o-galloyl-beta-d-glucose, interferon inducible protein, p21 (recombinant), peptide nucleic acid-DNA decoys, pentoxifylline (1-(5'-oxohexyl) 3,7-dimethylxanthine, peptide yy, pepluanone, perindopril, 6(5h)-phenanthridinone and benzamide, phenyl-n-tert-butylnitrone, phyllanthus amarus extracts, protein inhibitor of activated stat1, pioglitazone, pirfenidone, polyozellin, prenylbisabolane 3, pro-opiomelanocortin, prostaglandin e2, protein-bound polysaccharide, pypaf1 protein, pyridine n-oxide derivatives, pyrithione, quinadril, quinic acid, raf kinase inhibitor protein, rapamycin, raloxifene, raxofelast, rebamipide, *rhus verniciflua* stokes fruits 36 kda glycoprotein, ribavirin, rifamides, ritonavir, rosiglitazone, sanggenon c, santonin diacetoxy acetal derivative, secretory leucoprotease inhibitor, n-(p-coumaroyl) serotonin, sesamin, simvastatin, sinomenine, sirt1 deacetylase overexpression, siva-1, sm-7368, solana nigrum 1,150 kda glycoprotein, sun c8079, *tanacetum larvatum* extract, tansinones, taurine+niacine, thiazolidinedione mcc-555, trichostatin α, triclosan plus cetylpyridinium chloride, triptolide, tyrphostin ag-126, uteroglobin, vascular endothelial growth factor, verapamil, withaferin α, 5,7-dihydroxy-8-methoxyflavone, xylitol, yangan-wan, yin-chen-hao, yucca schidigera extract, amp-activated protein kinase, apc0576, *artemisia sylvatica*, bsasm, bifodobacteria, *bupleurum fruticosum* phenylpropanoids, ebv protein, chromene derivatives, dehydroevodiamine, 4'-demethyl-6-methoxypodophyllotoxin, ethyl 2-[(3-methyl-2,5-dioxo(3-pyrrol inyl))amino]-4-(trifluoromethyl)pyrimidine-5-carboxylate, cycloprodigiosin hycrochloride, dimethylfumarate, *fructus benincasae recens* extract, glucocorticoids (dexametasone, prednisone, methylprednisolone), gypenoside xlix, histidine, HIV-1 protease inhibitors (nelfinavir, ritonavir, or saquinavir), 4-methyl-1-(3-phenyl-propyl)-benzene-1,2-diamine, kwei ling ko, *ligusticum chuanxiong* hort root, nobiletin, NFκB repression factors, phenethylisothiocyanate, 4-phenylcoumarins, phomol, pias3, pranlukast, psychosine, quinazolines, resveratrol; ro31-8220, saucerneol d and saucerneol e, sb203580, tranilast, 3,4,5-trimethoxy-4'-fluorochalcone, *uncaria tomentosum* plant extract, mesalamine, mesuol, pertussis toxin binding protein, 9-aminoacridine derivatives (including the antimalaria drug quinacrine), adenosine and cyclic amp, 17-allylamino-17-demethoxygeldanamycin, 6-amino-quinazoline derivatives, luteolin, manassantins α and β, paromyxovirus sh gene products, qingkailing, shuanghuanglian, *smilax bockii* warb extract, tetracyclic a, tetrathiomolybdate, trilinolein, troglitazone, *witheringia solanacea* leaf extracts, wortmannin, α-zearalenol, antithrombin, rifampicin, and mangiferin. The presently disclosed invention can be especially beneficial because pain patients treated with protein-based cytokine inhibitors (for example and without limitation, etanercept or infliximab) often have immune responses directed against the recombinant (therapeutic) proteins. In the present invention, it is unlikely that there will be a significant immune response against a small molecule therapeutic compound.

The present invention can be used to treat a variety of conditions related to NFκB activation and pro-inflammatory cytokine responses. For example, embodiments according to the present invention could be used to contribute to the treatment of without limitation, osteoarthritis, alkylosing spondylitis, psoriasis, rheumatoid arthritis (RA), sepsis and degenerative disc disease. Further, it may be beneficial to coat implantable medical devices such as, without limitation, stents and stent graft with small molecule NF□B pathway inhibitors.

In one embodiment according to the present invention, the therapeutic agents described herein are delivered locally in order to minimize undesirable side effects associated with systemic delivery of the immunosuppressive agents. When delivered to local sites containing cells that have a responsive NFκB pathway, the therapeutic agents can be delivered through a device consisting of an infusion pump and a catheter. Local sites of delivery can include, but are not limited to the nerve root, the dorsal root ganglion (DRG), and focal sites of inflammation (containing infiltrating inflammatory cells). The distal, delivery end of the catheter can be surgically positioned in the tissue in close proximity to the targeted site (nerve root, DRG, etc). Alternatively, the distal end of the catheter may be positioned to deliver the therapeutic compound into the intrathecal space of the spinal cord. For acute therapeutic compound delivery, the proximal end of the catheter could remain outside of the patient's body and be attached to an external, refillable pump. For chronic administration of the compound, the proximal end of the catheter could be attached to a pump implanted subcutaneously within a patient. In this case, the pump would be able to be periodically refilled using transcutaneous syringe injection.

The NFκB inhibitors can be locally delivered by catheter and drug pump systems, delivered by direct local injection or through the use of polymers and/or drug-eluting stents as described in co-pending U.S. patent application Ser. No. 10/972,157 which is incorporated by reference herein. In one embodiment, a "controlled administration system" including a direct and local administration system can be used. A controlled administration system can be a depot or a pump system, such as, without limitation, an osmotic pump or an infusion pump. An infusion pump can be implantable and can be, without limitation, a programmable pump, a fixed rate pump, and the like. A catheter can be operably connected to the pump and configured to deliver agents of the present invention to a target tissue region of a subject. A controlled administration system can be a pharmaceutical depot (a pharmaceutical delivery composition) such as, without limitation, a capsule, a microsphere, a particle, a gel, a coating, a matrix, a wafer, a pill, and the like. A depot can comprise a biopolymer. The biopolymer can be a sustained-release biopolymer. The depot can be deposited at or near, generally in close proximity, to a target site. Embodiments of the present invention also can be delivered through the use of liposomes, polyethyleneimine, by iontophoresis, or by incorporation into other vehicles, such as biodegradable or non-biodegradable nanocapsules. The delivery technology (drug pump or polymer formulations) can also be useful for the delivery of small molecules directed against other gene targets for other clinical indications.

The present invention also includes kits. In one embodiment, the kits of the present invention comprise NFκB inhibitors of the present invention. In another embodiment, a kit of the present invention can contain one or more of the following in a package or container: (1) one or more NFκB inhibitors of the present invention; (2) one or more pharmaceutically acceptable adjuvants or excipients; (3) one or more vehicles for administration, such as one or more syringes; (4) one or more additional bioactive agents for concurrent or sequential administration; (5) instructions for administration; and/or (6) a catheter and drug pump. Embodiments in which two or more of components (1)-(6) are found in the same container can also be used.

When a kit is supplied, the different components of the compositions included can be packaged in separate containers and admixed immediately before use. Such packaging of the components separately can permit long-term storage without losing the active components' functions. When more than one bioactive agent is included in a particular kit, the bioactive agents may be (1) packaged separately and admixed separately with appropriate (similar or different) vehicles immediately before use, (2) packaged together and admixed together immediately before use or (3) packaged separately and admixed together immediately before use. If the chosen compounds will remain stable after admixture, however, the admixture need not occur immediately before use but can occur at a time before use, including in one example, minutes, hours, days, months or years before use or in another embodiment at the time of manufacture.

The compositions included in particular kits of the present invention can be supplied in containers of any sort such that the life of the different components are preserved and are not adsorbed or altered by the materials of the container. For example, sealed glass ampules can contain lyophilized agents or variants or derivatives thereof or other bioactive agents, or buffers that have been packaged under a neutral, non-reacting gas, such as, without limitation, nitrogen. Ampules can consist of any suitable material, such as, without limitation, glass, organic polymers, such as, polycarbonate, polystyrene, etc., ceramic, metal or any other material typically employed to hold similar reagents. Other examples of suitable containers include, without limitation, simple bottles that may be fabricated from similar substances as ampules, and envelopes, that can comprise foil-lined interiors, such as aluminum or an alloy. Other containers include, without limitation, test tubes, vials, flasks, bottles, syringes, or the like. Containers can have one or more sterile access ports, such as a bottle having a stopper that can be pierced by a hypodermic injection needle. Other containers may have two compartments that are separated by a readily removable membrane that upon removal permits the components to be mixed. Removable membranes may be, without limitation, glass, plastic, rubber, etc.

As stated earlier, kits can also be supplied with instructional materials. Instructions may be printed on paper or other substrate, and/or may be supplied as an electronic-readable medium, such as a floppy disc, CD-ROM, DVD-ROM, Zip disc, videotape, audiotape, flash memory device, etc. Detailed instructions may not be physically associated with the kit; instead, a user may be directed to an internet web site specified by the manufacturer or distributor of the kit, or supplied as electronic mail.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Certain embodiments of this invention are described herein, including the best mode known to the inventors for carrying out the invention. Of course, variations on these certain embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of treating pain comprising: administering one or more depots containing clonidine and a statin locally to a target tissue site causing pain in a patient in need thereof to inhibit pro-inflammatory cytokines associated with pain, wherein the pain comprises at least one of acute pain, neuropathic pain, pain from sciatica, or radicular pain.

2. A method according to claim 1 wherein said one or more depots comprise a biodegradable polymer containing PLGA (polylactide-co-glycolide) that provides sustained release of the clonidine.

3. A method according to claim 1 wherein one or more depots comprise microspheres containing the clonidine.

4. A method according to claim 1 wherein said one or more depots containing the clonidine are administered locally to the perispinal region of the lumbar region of a spinal cord or are administered locally to the epidural space or the intrathecal space of the lumbar region of a spinal cord.

5. A method according to claim 1 wherein said one or more depots containing the clonidine are administered locally from an administration route selected from the group consisting of a catheter and drug pump, one or more local injections, polymer release, and combinations thereof.

6. A method according to claim 1 wherein said pain is acute pain.

7. A method according to claim 1 wherein said pain is from sciatica.

8. A dosing regimen comprising one or more depots containing clonidine and a statin and instructional information that directs the administration of said one or more depots for the local treatment of pain, wherein the pain comprises at least one of acute pain, neuropathic pain, pain from sciatica, or radicular pain.

9. A dosing regimen according to claim 8 wherein said one or more depots comprise a polymer and clonidine disposed in the polymer, wherein the polymer allows sustained release of the clonidine.

10. A dosing regimen according to claim 8 wherein said one or more depots contain a polymer comprising PLGA (polylactide-co-glycolide) and the instructional information directs said one or more depots to be administered locally to the perispinal region of the lumbar region of a spinal cord or to be administered locally to the epidural space or the intrathecal space of the lumbar region of a spinal cord.

11. A dosing regimen according to claim 8 wherein said instructional information directs said one or more depots containing the clonidine to be administered locally from an administration route selected from the group consisting of a catheter and drug pump, one or more local injections, polymer release, and combinations thereof.

12. A dosing regimen according to claim 8 wherein said instructional information directs said one or more depots containing the clonidine to be administered for the treatment of acute or neuropathic pain.

13. A dosing regimen according to claim 8 wherein said instructional information directs said one or more depots containing the clonidine to be administered for the treatment of sciatica or radicular pain.

14. A dosing regimen according to claim 8 wherein said dosing regimen is part of a kit used for the treatment of pain.

* * * * *